United States Patent [19]

Suzuki et al.

[11] Patent Number: 5,110,498
[45] Date of Patent: May 5, 1992

[54] LIQUID CRYSTAL COMPOUND

[75] Inventors: Yoshiichi Suzuki; Shigenori Sakuma; Noriko Yamakawa, all of Tokyo, Japan

[73] Assignee: Showa Shell Sekiyu K.K., Tokyo, Japan

[21] Appl. No.: 634,631

[22] Filed: Dec. 27, 1990

[30] Foreign Application Priority Data

Dec. 27, 1989 [JP] Japan ................................. 1-339481

[51] Int. Cl.$^5$ ...................... C09K 19/12; C09K 19/34; C09K 19/20
[52] U.S. Cl. ..................... 252/299.66; 252/299.67; 252/299.61; 252/299.62; 252/299.63; 560/64; 560/65; 560/83
[58] Field of Search ...................... 252/299.66, 299.67, 252/299.62, 299.61, 299.63; 560/64, 65, 83

[56] References Cited

U.S. PATENT DOCUMENTS

| | | | |
|---|---|---|---|
| 4,770,503 | 9/1988 | Buchecker et al. | 350/350 R |
| 4,871,472 | 10/1989 | Krause et al. | 252/299.65 |
| 4,898,455 | 2/1990 | Buchecker et al. | 350/350 R |
| 4,906,401 | 3/1990 | Dübal et al. | 252/299.61 |
| 4,906,752 | 3/1990 | Müller, et al. | 544/318 |
| 4,917,817 | 4/1990 | Nohira et al. | 252/299.01 |
| 4,917,821 | 4/1990 | Mori et al. | 252/299.63 |
| 4,918,213 | 4/1990 | Nohira et al. | 558/271 |
| 4,921,632 | 5/1990 | Nakamura et al. | 252/299.1 |

FOREIGN PATENT DOCUMENTS

| | | | |
|---|---|---|---|
| 0330491 | 8/1989 | European Pat. Off. | |
| 0332392 | 9/1989 | European Pat. Off. | |
| 2612182 | 10/1988 | France | 560/65 |
| 61-027931 | 2/1986 | Japan | 562/299.65 |
| 1227547 | 10/1986 | Japan | 560/83 |

Primary Examiner—Robert L. Stoll
Assistant Examiner—C. Harris
Attorney, Agent, or Firm—Sughrue, Mion, Zinn, Macpeak & Seas

[57] ABSTRACT

A liquid crystal compound represented by formula (I):

$$R_2-X-(A)-Y-(B)-COO-\overset{R_3}{\underset{*}{C}H}-R_1 \quad (I)$$

wherein $R_1$ represents an alkyl group having from 3 to 18 carbon atoms or an aralkyl group having from 7 to 18 carbon atoms; $R_2$ represents an alkenyl group having from 1 to 18 (preferably from 3 to 14) carbon atoms; $R_3$ represents $CF_3$ or $C_2F_5$; X represents a single bond, —O—, —COO—, or —OCO—; Y represents —COO—, —OCO—, —CH$_2$O—, or —OCH$_2$—; A and B each represents a cyclic group; and * indicates an optically active center.

The compound of formula (I) exhibits three stable states of molecular orientation.

8 Claims, 7 Drawing Sheets

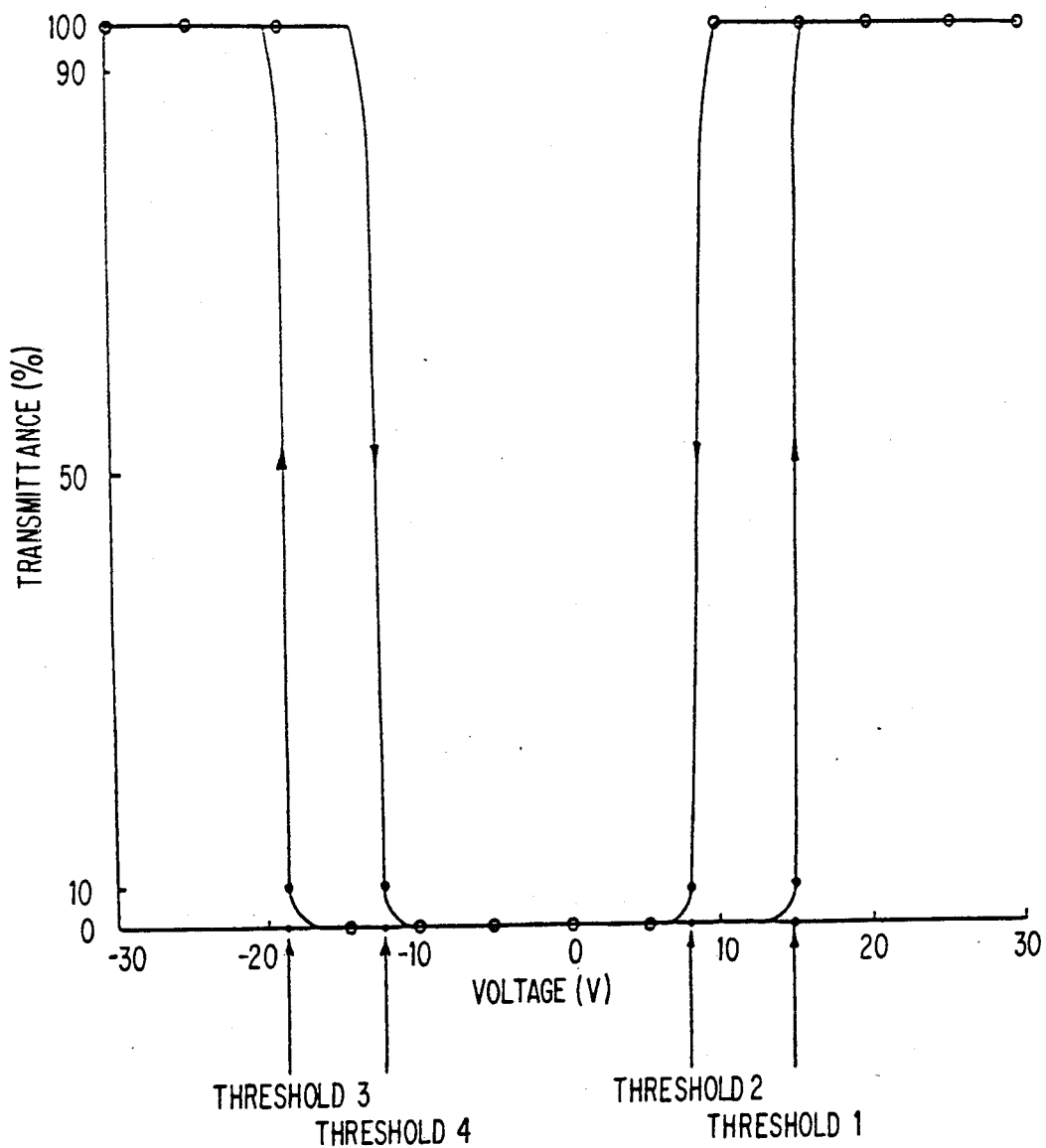

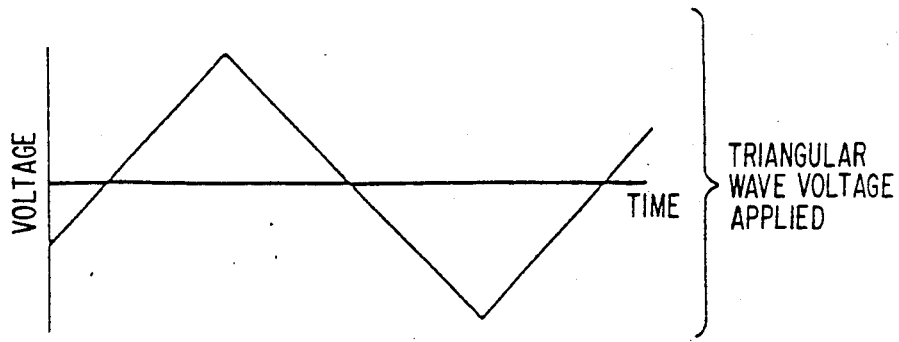
FIG. 4(A) — TRIANGULAR WAVE VOLTAGE APPLIED
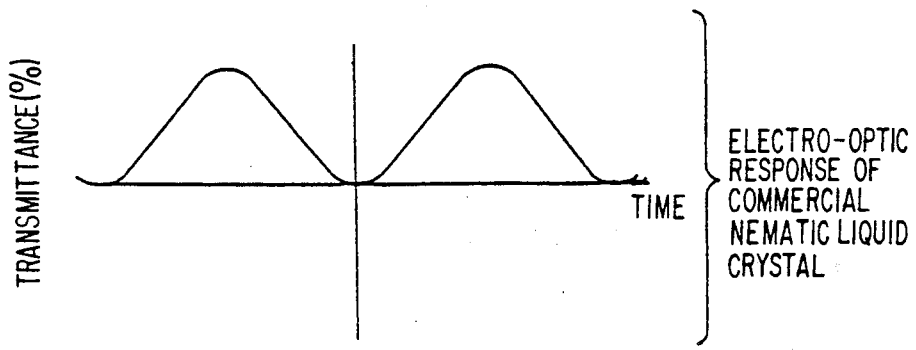
FIG. 4(B) — ELECTRO-OPTIC RESPONSE OF COMMERCIAL NEMATIC LIQUID CRYSTAL
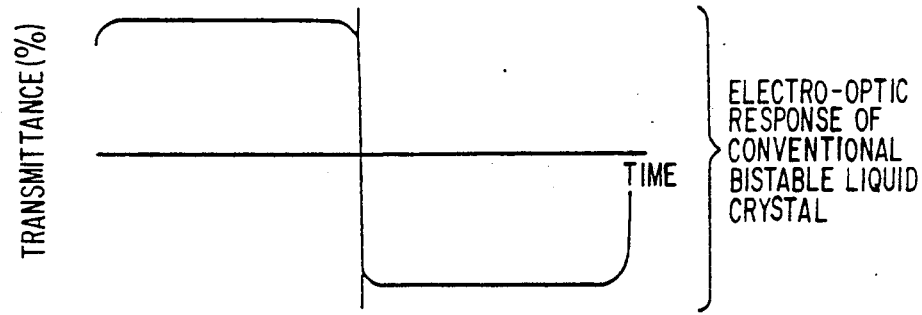
FIG. 4(C) — ELECTRO-OPTIC RESPONSE OF CONVENTIONAL BISTABLE LIQUID CRYSTAL
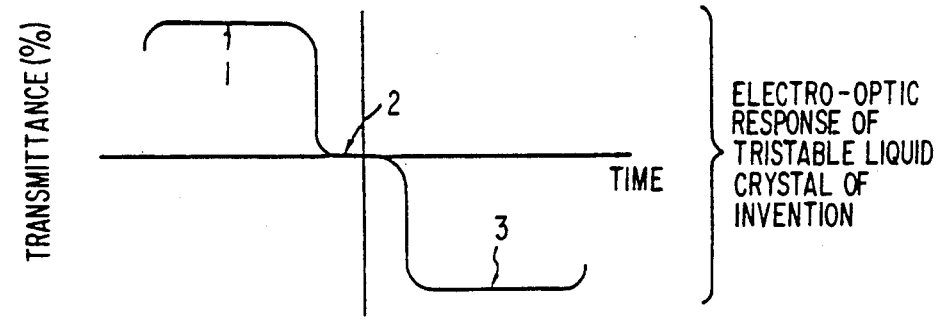
FIG. 4(D) — ELECTRO-OPTIC RESPONSE OF TRISTABLE LIQUID CRYSTAL OF INVENTION

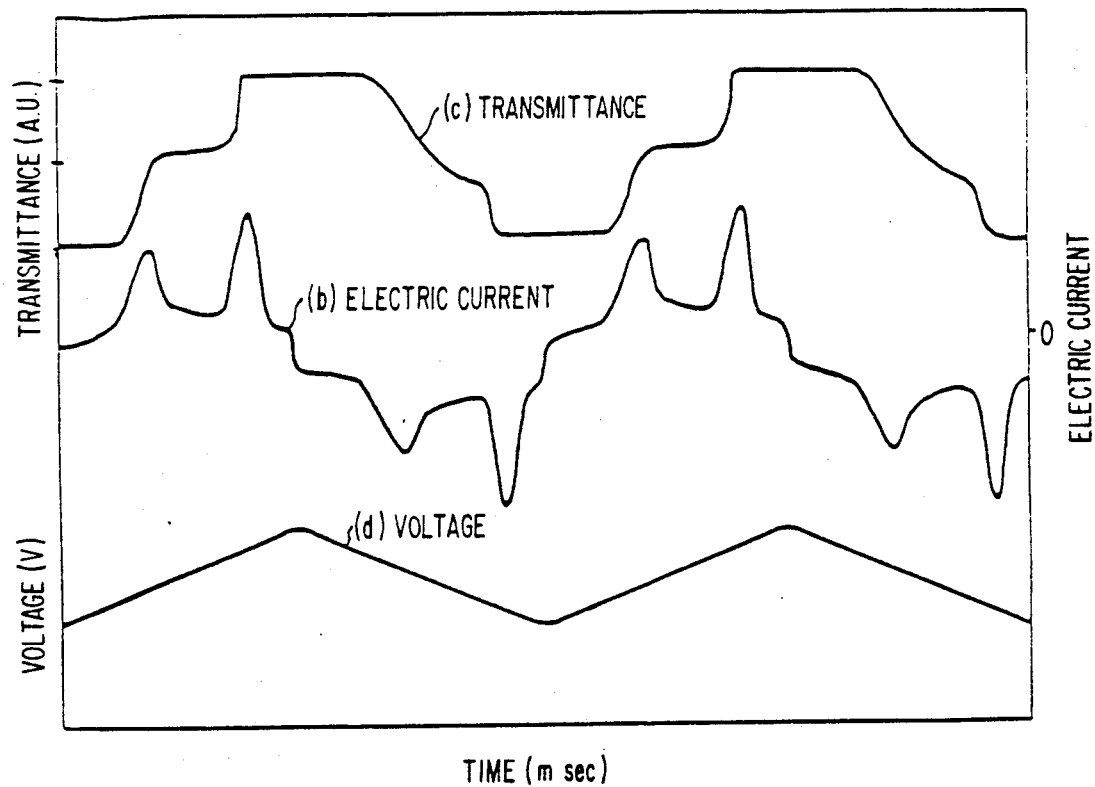

LIQUID CRYSTAL COMPOUND

FIELD OF THE INVENTION

This invention relates to a novel halogen-containing liquid crystal compound comprising an ester or ether of an optically active halogen-containing alcohol.

All the liquid crystal compounds of this invention are ferroelectric liquid crystal compounds exhibiting bistable states, and furthermore, the liquid crystal compounds of this invention (those wherein the haloalkyl group thereof is $CF_3$ or $C_2F_5$) are ferroelectric liquid crystal compounds of novel type which exhibit three stable (tristable) states.

BACKGROUND OF THE INVENTION

Electro-optic devices using liquid crystals which have been developed and put into practical use to date include those using nematic liquid crystals, such as a DSM mode, a TN mode, a G-H mode, and an STN mode. However, such devices using nematic liquid crystals have a very slow electro-optic response and require a switching time from several milliseconds to several tens of milliseconds and are thus limited in their range of application. The slow response of these elements using nematic liquid crystals is due to the fact that the torque of moving molecules, which is basically based on anisotropy of their dielectric constant, is not very high.

In light of the above, Meyer et.al. developed ferroelectric liquid crystals which undergo spontaneous polarization (Ps) which have a strong torque, the torque being based on PsxE (the applied electric field), and which thus have a high speed response in the order of microseconds, as disclosed in Le Journal de Physique, Vol. 36, L-69 (1975). Further, JP-A-63-307837 (the term "JP-A" as used herein means an "unexamined published Japanese patent application") discloses new ferroelectric liquid crystals, but has no disclosure on the "three states" concept hereinafter discussed.

Several high speed electro-optic devices using ferroelectric liquid crystals have been proposed to date. Typically, such devices include an element in which a twisted structure is untwisted by the force of wall surfaces, and two direction of molecular by changing the polarity of an applied electric field as described, e.g., in JP-A-56-107216.

The use of a compound showing ideal two states having an electric field response waveform as shown in FIG. 1 is prerequisite in the above-described devices. However, such a compound exhibiting ideal two (bistable) states is not yet available. The so far synthesized bistable liquid crystals have a response waveform as shown in FIG. 2, not as shown in FIG. 1. When the state-of-the-art liquid crystals having a response waveform as shown in FIG. 2 are used, for example, in light switching circuits, since transmission gradually changes as the applied voltage changes from negative to positive, the desired results cannot be sufficiently achieved simply by changing the applied voltage between "on" and "off". Moreover, currently available bistable liquid crystals have difficulty in reaching a mono-domain state in their Sc* phase without an applied voltage, i.e., in reaching an ideal molecular orientation state, and easily undergo defect or a molecular orientation disturbance called twist. Thus, it has been difficult to achieve the above-stated ideal two states of molecular orientation over a wide range.

Further, because the threshold value (voltage at which luminance changes by a prescribed value) is low, dynamic driving is liable to suffer from a reduction in contrast or a reduction in the viewing angle.

Furthermore, these conventional bistable liquid crystals do not exhibit a hysteresis loop as shown in FIG. 1, but exhibit hysteresis as shown in FIG. 2 so that they have no memory effect. Therefore, it is necessary to continue applying a voltage of $v_3$ as shown in FIG. 2 or continue applying a high frequency for the liquid crystal to maintain a stable response in the Sc* phase, which, in either case, results in a considerable energy consumption.

Thus, conventional electro-optic devices have many defects which need to be overcome, notwithstanding the strong demand for devices which make effective use of the characteristics of electro-optic devices to use an applied electric field to achieve molecular orientation of ferroelectric liquid crystals.

SUMMARY OF THE INVENTION

An object of this invention is to provide not only a novel liquid crystal compound which exhibits two states, but also a novel liquid crystal compound which exhibits stable three molecular orientation (tristable) states having a high light/shade contrast in the absence of an electric field, which has well defined threshold characteristics and a well defined hysteresis curve or loop as shown in FIG. 3, which easily undergoes dynamic driving, and which can be used in liquid crystal electro-optic devices utilizing three states, which make it possible to obtain a high-speed response.

More specifically, an object of this invention is to provide a novel bistable liquid crystal compound.

Another object of this invention is to provide a novel ferroelectric chiral smectic liquid crystal compound exhibiting three stable molecular orientation states which are entirely different from a chiral smectic C phase (Sc* phase) which is a conventional bistable state phase.

The terminology "three states" as used herein means stable three molecular orientation states as now explained. In a liquid crystal electro-optic device comprising a pair of electrode substrates with a prescribed gap therebetween and a ferroelectric liquid crystal sandwiched between the pair of substrates, the electrodes being connected to an electric power source so that voltage of triangular wave as shown in FIG. 4(A) can be applied thereto, the ferroelectric liquid crystal shows a first stable molecular orientation state as shown by numeral 2 of FIG. 4(D) when no electric field is applied thereto, a second stable molecular orientation state as shown by numeral 1 of FIG. 4(D) differing from the first stable state when an electric field is applied to one direction, and a third stable molecular orientation state as shown by numeral 3 of FIG. 4(D) differing from either of the first and second stable states when an electric field is applied in a direction opposite the first direction. With respect to liquid crystal electro-optic devices utilizing these three stable states, the inventors have already filed JP-A-2-153322.

On the contrary, "commercially available nematic liquid crystals" and so far synthesized bistable liquid crystals do not have such three stable states, but exhibit states as shown in FIGS. 4(B) and (C), respectively.

The above ferroelectric liquid crystals having three states (hereinafter sometimes referred to as tristable liquid crystals) according to the present invention produce striking effects when applied to liquid crystal displays as compared with conventional nematic liquid crystals, as discussed.

While conventional liquid crystals must be driven using a very complicated system called an active matrix system, the tristable ferroelectric liquid crystals of the present invention can be driven using a simple matrix display. Accordingly, a display element using the tristable ferroelectric liquid crystal can be produced in a simple manner, which makes it feasible to widen the display area and to reduce production costs, whereas conventional display elements require complicated production steps, encounter difficulty in widening the display area, and involve high production costs.

The present invention provides a liquid crystal compound represented by formula (I):

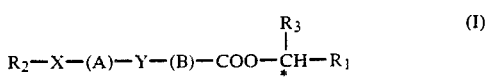

wherein $R_1$ represents an alkyl group having from 3 to 18 carbon atoms or an aralkyl group having from 7 to 18 carbon atoms; $R_2$ represents an alkenyl group having from 1 to 18 (preferably from 3 to 14) carbon atoms; $R_3$ represents $CF_3$ or $C_2F_5$; X represents a single bond, $-O-$, $-COO-$, or $-OCO-$; Y represents $-COO-$, $-OCO-$, $-CH_2O-$, or $-OCH_2$; A and B each represents a cyclic group; and * indicates an optically active center.

BRIEF DESCRIPTION OF THE DRAWINGS

FIGS. 1, 2, and 3 each shows the hysteresis curve or loop of an ideal bistable liquid crystal (which is not actually available), of a conventionally synthesized bistable liquid crystal, and of a tristable liquid crystal according to the present invention, respectively, in which the applied voltage is plotted as the abscissa and the transmittance (%) as the ordinate.

FIG. 4(A) shows the triangular wave applied.

FIGS. 4(B), (C), and (D) each shows the electro-optic response of a commercially available nematic liquid crystal, a conventionally synthesized bistable liquid crystal, and a tristable liquid crystal according to the present invention, respectively, when the triangular wave of FIG. 4(A) is applied.

FIG. 5 illustrates switching among the three states of a compound according to the present invention, in which (a) is the triangular voltage wave applied to the liquid crystal electro-optic element, (b) is the polarization inversion current; and (c) is the transmission change with the voltage (a).

In FIG. 7, the triangular wave of straight line is an applied voltage. The abscissa indicates time, and the ordinate indicates voltage for the triangular wave or transmittance (transmitted light intensity) (A.U.) for the curve.

DETAILED DESCRIPTION OF THE INVENTION

Figure 1:
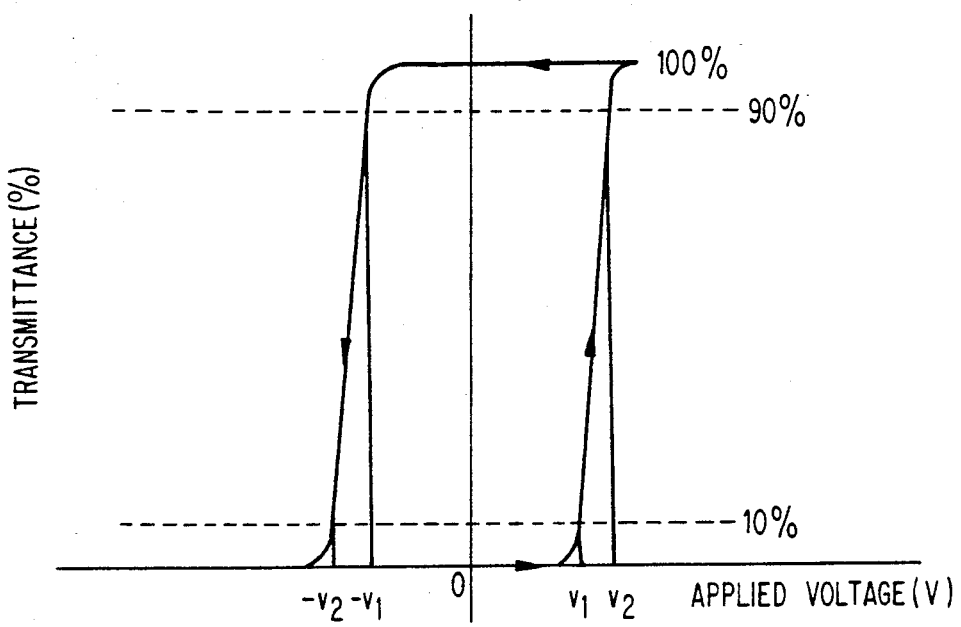
Figure 2:
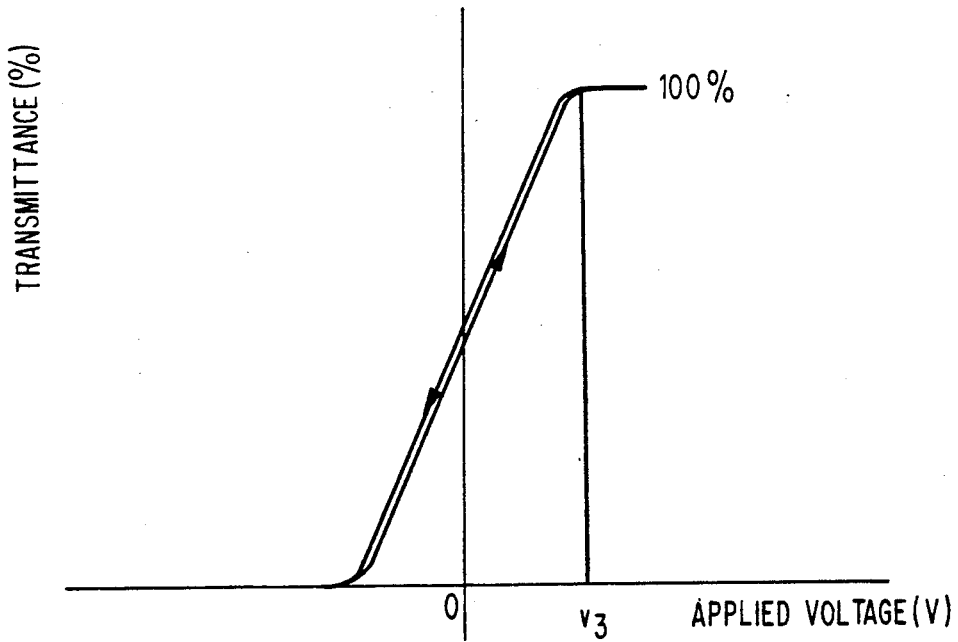

In formula (I), specific examples of the cyclic group as represented by A or B are shown below. In the following groups, one or two hydrogen atoms may be substituted by a halogen atom(s).

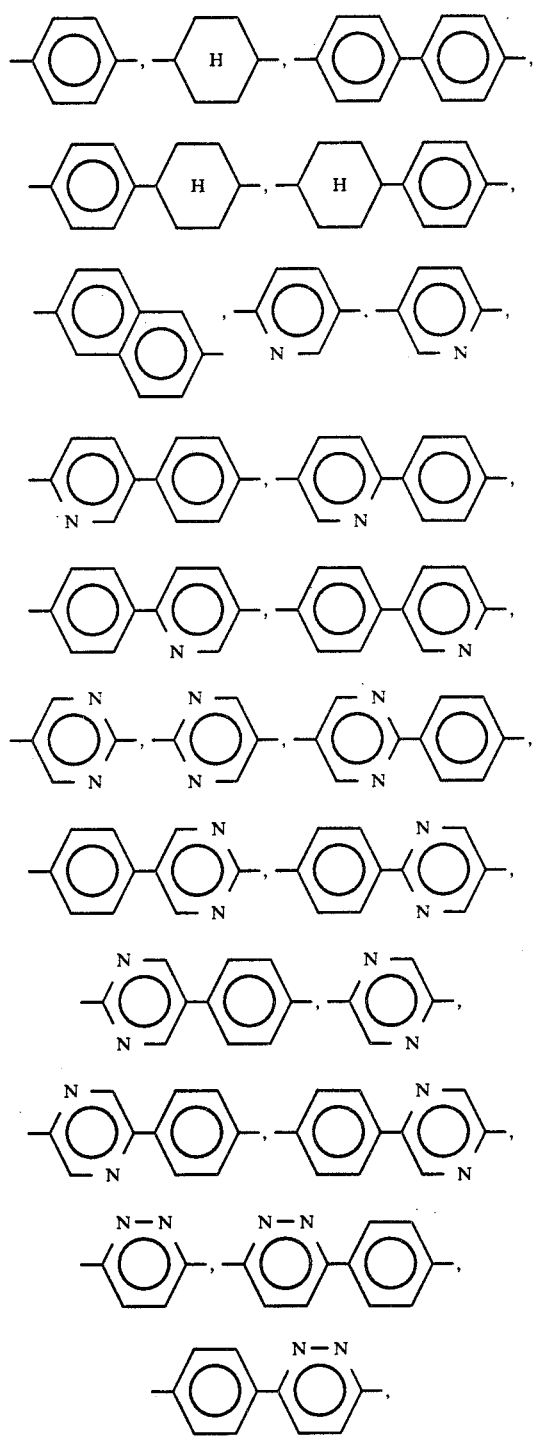

Of the liquid crystal compounds represented by formula (I) preferred are those represented by formula:

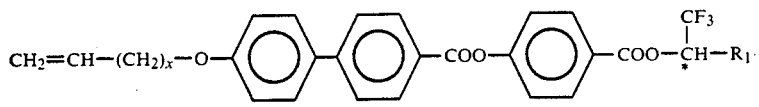

wherein $R_1$ is as defined above; and x is an integer of from 1 to 12.

The compounds according to the present invention can be synthesized by starting with an optically active haloalkanol represented by formula (II):

wherein $R_1$ and $R_3$ are as defined above.

Examples of optically active halogen-containing alcohols which can be preferably used in the present invention are 1,1,1-trifluoro-2-hexanol, 1,1,1-tri-fluoro-2-nonanol, 1,1,1-trifluoro-2-decanol, 1,1,1-fluoro-2-undecanol, 1,1,1-trifluoro-2-dodecanol, 1,1,1-trifluoro-2-tridecanol, 1,1,1-trifluoro-2-tetra-decanol, 1,1,1-trifluoro-2-pentadecanol, 1,1,1-tri-fluoro-2-hexadecanol, 1,1,1-trifluoro-2-heptadecanol, and 1,1,1-trifluoro-2-octadecanol. The above-enumerated halogen-containing alcohols with the trifluoro group replaced with a monofluoro group, difluoro group, a pentafluoro group, or a dichloromonofluoro group are also preferred.

The starting alcohol represented by formula (II) can be obtained by asymmetric synthesis, optical resolution or the like technique. When, in particular, a compound having high optical purity is desired, processes using enzymes, yeasts or bacteria are effective. In a typical example, the alcohol can be synthesized according to the reaction scheme illustrated below.

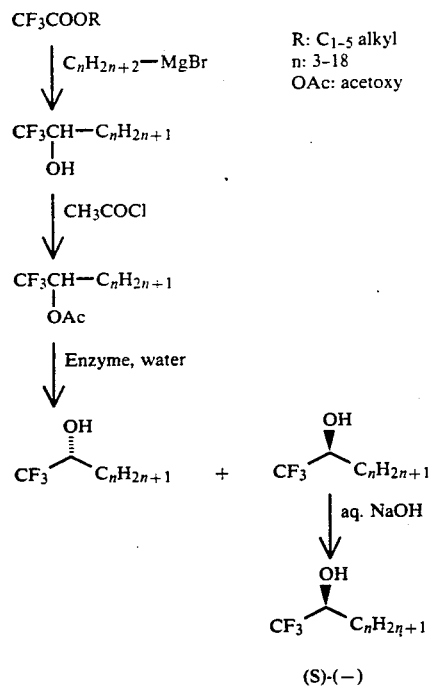

Ethyl trifluoroacetate and a Gringnard reagent of an alkyl bromide are reacted to obtain a trifluoroalkyl ketone. The ketone is reduced with sodium borohydride to obtain a 1-trifluoro-2-alkanol, which is then converted to an acetate ester. The ester is stereo-selectively hydrolyzed in the presence of yeast or bacteria to obtain an optically active (R)- or (S)-compound of a 1-trifluoro-2-alkanol.

In the above synthesis, ethyl trifluoroacetate may be replaced with ethyl monofluoroacetate, ethyl difluoroacetate, ethyl pentafluoroacetate or ethyl trichloroacetate to obtain the corresponding optically active 1-haloalkyl-2-alkanol.

An example of synthesizing the liquid crystal compound of the present invention is illustrated below.

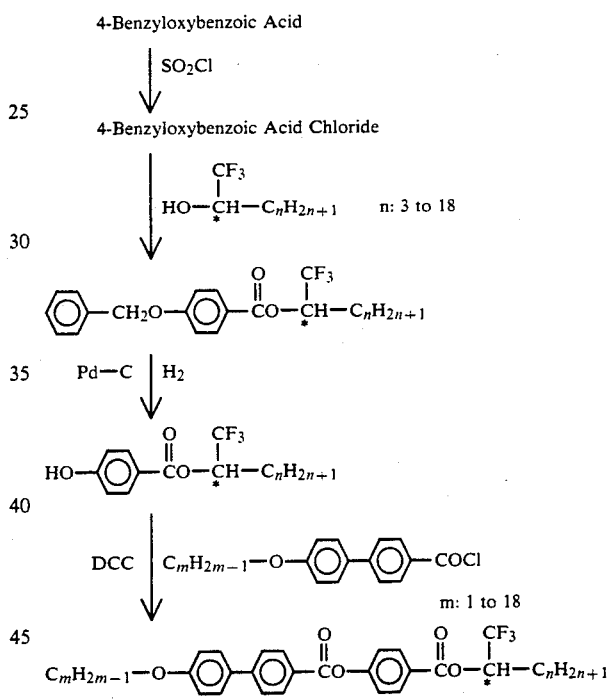

4-Benzyloxybenzoic acid is converted to its acid chloride with a chlorinating reagent, e.g., thionyl chloride, which is then reacted with an (R)-(+)- or (S)-(−)-trifluoro-2-alkanol to obtain an ester. The ester is subjected to debenzylation, and the resulting phenol compound is reacted with a chloride of a 4-alkyloxy-4'-biphenylcarboxylic acid to obtain a desired compound.

The liquid crystal compounds of the present invention can also be synthesized by dehydrating condensation between a 4-alkyl- or 4-alkoxy-4'-biphenylcarboxylic acid and a phenol derivative of an optically active haloalkanol in the presence of a condensing agent, e.g., dicyclohexylcarbodiimide (DCC).

Specific examples of the liquid crystal compounds according to the present invention are shown below.
(1) 4-Alkenyl-4'-biphenylcarboxylic acid 4-(1,1,1-trifluoro-2-hexyloxycarbonyl)phenyl ester
(2) 4-Alkenyl-4'-biphenylcarboxylic acid 4-(1,1,1-trifluoro-2-heptyloxycarbonyl)phenyl ester
(3) 4-Alkenyl-4'-biphenylcarboxylic acid 4-(1,1,1-trifluoro-2-octyloxycarbonyl)phenyl ester (4) 4-Alkenyl-4'-biphenylcarboxylic acid 4-(1,1,1-trifluoro-2-nonyloxycarbonyl)phenyl ester
(5) 4-Alkenyl-4'-biphenylcarboxylicacid 4-(1,1,1-trifluoro-2-undecyloxycarbonyl)phenyl ester
(6) 4-Alkenyl-4'-biphenylcarboxylic acid 4-(1,1,1-trifluoro-2-dodecyloxycarbonyl)phenyl ester
(7) 4-Alkenyl-4'-biphenylcarboxylic acid 4-(1,1,1-trifluoro-2-tridecyloxycarbonyl)phenyl ester
(8) 4-Alkenyl-4'-biphenylcarboxylic acid 4-(1,1,1-trifluoro-2-tetradecyloxycarbonyl)phenyl ester
(9) 4-Alkenyl-4'-biphenylcarboxylic acid 4-(1,1,1-trifluoro-2-pentadecyloxycarbonyl)phenyl ester
(10) 4-Alkenyl-4'-biphenylcarboxylic acid 4-(1,1,1-trifluoro-2-hexadecyloxycarbonyl)phenyl ester
(11) 4-Alkenyl-4'-biphenylcarboxylic acid 4-(1,1,1-trifluoro-2-heptadecyloxycarbonyl)phenyl ester
(12) 4-Alkenyl-4'-biphenylcarboxylic acid 4-(1,1,1-trifluoro-2-heptadecyloxycarbonyl)phenyl ester
(13) 4-Alkenyl-4'-biphenylcarboxylic acid 4-(1,1,1-trifluoro-2-octadecyloxycarbonyl)phenyl ester The optically active compounds and their liquid crystal derivatives embrace (R)-compounds and (S)-compounds. While not limited, the higher the optical purity, the better.

There are three factors which determine whether or not the liquid crystal compound represented by formula (I) exhibits satisfactory three stable states as follows.

(i) Where X or Y, especially Y, is an ester bond, it is desirable for manifestation of three stable states that the direction of the ester is the same as that of the ester bonded to the left-hand side of the asymmetric carbon atom.

(ii) It is desirable for manifestation of three stable states that either one of (A) and (B) is a biphenyl group, with the other being a phenylene group. exhibited when the fluoroalkyl group bonded to the asymmetric carbon atom in a $CF_3$ group.

The present invention is now illustrated in greater detail by way of Examples, but it should be understood that the present invention is not deemed to be limited thereto.

EXAMPLE 1

Synthesis of 4-(4-Pentenyloxy)biphenyl-4'-carbox-ylic acid 4-(1,1,1-trifluoro-2-octyloxycarbonyl)-phenyl ester:

In 20 ml of methylene chloride was dissolved 1.0 g of 4-benzyloxybenzoic acid chloride, and a solution of 0.67 g of optically active 1,1,1-trifluoro-2-octanol, 0.36 g of triethylamine, and a catalytic amount of dimethylaminopyridine in 10 ml of methylene chloride was slowly added thereto under ice-cooling. The reaction mixture was allowed to warm to room temperature, stirred at that temperature for 12 hours, poured into ice-water and extracted with methylene chloride. The methylene chloride phase was washed successively with diluted hydrochloric acid, water, an aqueous 1N sodium carbonate solution, and water and dried over anhydrous magnesium sulfate. The solvent was removed by distillation under reduced pressure to obtain a crude product. The crude product was purified by column chromatography using silica gel to obtain 0.65 g of 1,1,1-trifluoro-2-octyl 4-benzyloxybenzoate.

The resulting ester compound and 0.07 g of 10% palladium-on-carbon were added to ethanol to conduct debenzylation in a hydrogen atmosphere to obtain 0.48 g of 1,1,1-trifluoro-2-octyl 4-hydroxybenzoate.

To 10 ml of methylene chloride were added 0.48 g of 1,1,1-trifluoro-2-octyl 4-hydroxybenzoate, 0.16 g of triethylamine, and a catalytic amount of dimethylaminopyridine, and a solution of 0.57 g of 4-(4-pentenyloxy) biphenylcarboxylic acid chloride in 10 ml of methylene chloride was added slowly thereto under ice-cooling. The reaction mixture was allowed to warm to room temperature, followed by stirring for one day. The reaction mixture was poured into water and extracted with methylene chloride. The methylene chloride phase was washed successively with diluted hydrochloric acid, water, an aqueous 1N sodium carbonate solution, and water and dehydrated over anhydrous magnesium sulfate. The solvent was removed by distillation under reduced pressure, and the crude product was purified by column chromatography using silica gel to obtain 0.33 g of the titled compound ($[\alpha]_D^{20} = +34.3°$). The resulting compound exhibited liquid crystal characteristics. The phase transition temperatures of the liquid crystal compound obtained were measured by polarizing microscopic observation using temperature controlled hot stage in which a liquid crystal cell was placed. Phase Transition Temperatures (° C.):

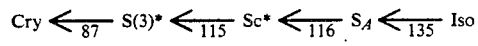

Figure 8:
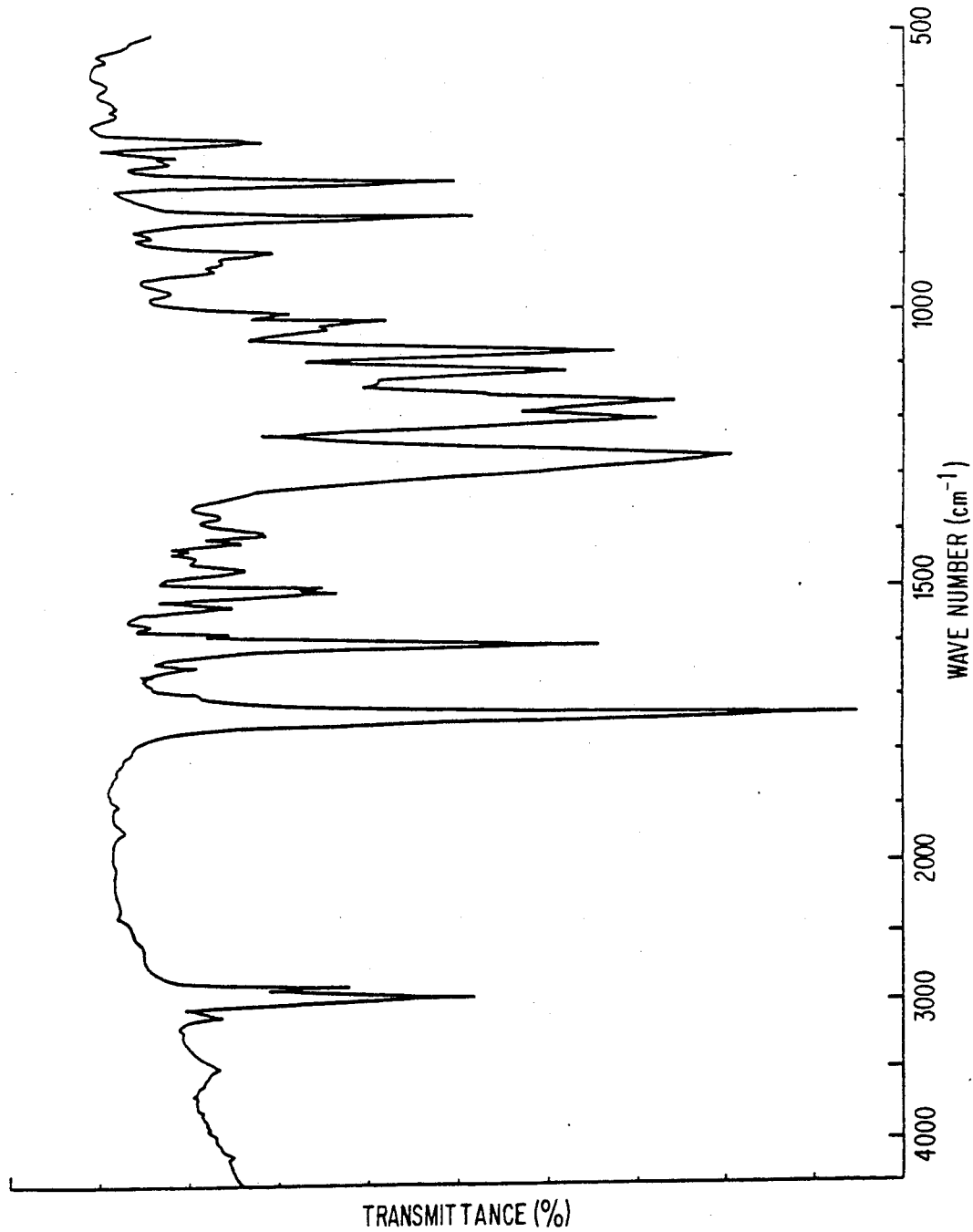
FIG. 8 shows the infrared absorption spectrum of the compound obtained in Example 1.

The infrared absorption spectrum (KBr) of the compound is shown in FIG. 8.

EXAMPLE 2

The liquid crystal compound obtained in Example 1 was filled, while in an isotropic phase, into a liquid crystal cell having a polyimide orientation film which had been subjected to a rubbing treatment on an ITO (indium tin oxide) electrode substrate (cell thickness: 2.7 μm).

The resulting cell was slowly cooled at a cooling rate of 0.1 to 1.0° C./min to orientate the liquid crystal molecules in an S(3)* phase. Cooling was continued, and a triangular wave voltage of ±30 V and 10 Hz was applied to the cell at 90° C.

The cell was set between a pair of cross polarizing sheets in such a manner that the direction of the molecular longer axis with no voltage applied was in parallel with one of the polarizing sheets, and changes of transmitted light intensity due to the change of the triangular wave voltage were observed. As shown in FIG. 3, a well defined threshold voltage and a double hysteresis loop were revealed.

Figure 6:
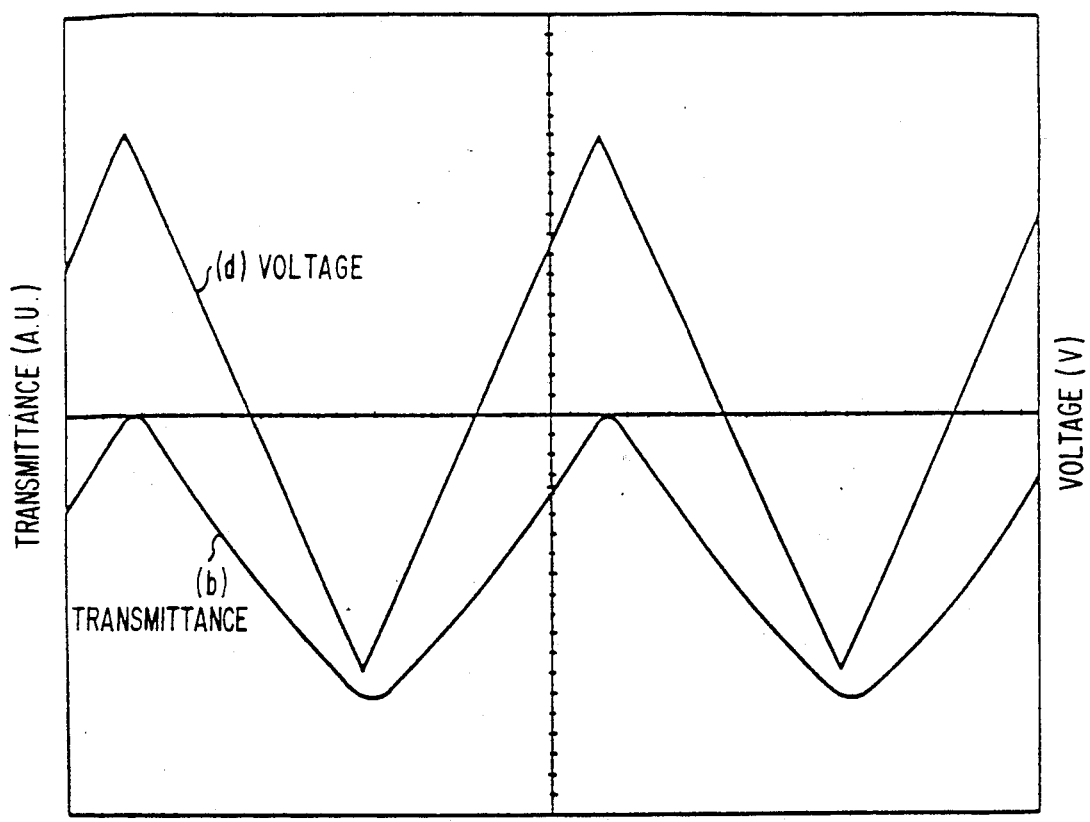
FIG. 6 shows an electro-clinic effect, in which (a) is an alternating voltage applied to a liquid crystal electro-optic element, and (b) shows the changes of transmittance with alternating voltage (a).
Figure 7:
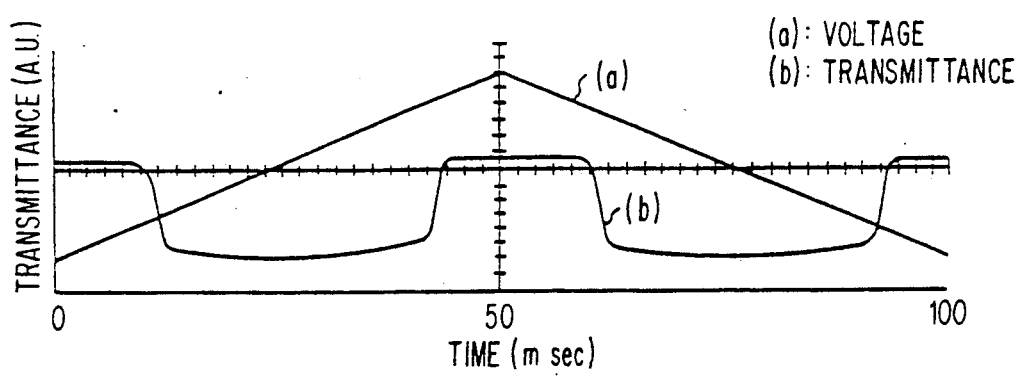
FIG. 7 shows the tristable response waveform of the novel liquid crystal compound obtained in Example 1.

As described above, the novel liquid crystal compounds of the present invention all exhibit bistability. They also exhibit an electro-clinic effect as illustrated in FIG. 6. The present invention makes conventionally available liquid crystal materials more useful and competent. In particular, the compounds of the present invention have a $CF_3$ group or a $C_2F_5$ group in the molecule thereof thereby exhibiting three stable states and can be utilized in a wide range of applications, such as in display devices and switching devices.

While the invention has been described in detail and with reference to specific embodiments thereof, it will be apparent to one skilled in the art that various changes and modifications can be made therein without departing from the spirit and scope thereof.

What is claimed is:

1. A liquid crystal compound represented by formula (I):

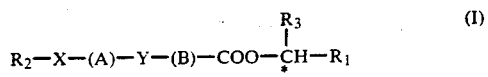

wherein $R_1$ represents an alkyl group having from 3 to 18 carbon atoms or an aralkyl group having from 7 to 18 carbon atoms; $R_2$ represents an alkenyl group having from 2 to 18 carbon atoms and containing a double bond at the terminal; $R_3$ represent $CF_3$ or $C_2F_5$; X represents a single bond, $-O-$, $-COO-$, or $-OCO-$; Y represents $-COO-$, $-OCO-$, $-CH_2O-$, or $-OCH_2-$; A and B each represent cyclic groups having 1 to 2 six-membered rings cyclic group or naphthalene; and * indicates an optically active center.

2. A liquid crystal compound as claimed in claim 1, wherein A and B are selected from the group consisting of homocyclic and nitrogen containing heterocyclic groups.

3. A liquid crystal compound as claimed in claim 1, wherein $R_2$ represents an alkenyl group having from 3 to 14 carbon atoms and containing a double bond at the terminal 4. A liquid crystal compound as claimed in claim 1, wherein X or Y is an ester bond, the direction of which is the same as that of the ester bonded to the left-hand side of the asymmetric carbon atom constituting the optically active center.

5. A liquid crystal compound as claimed in claim 1, wherein one of (A) and (B) is a biphenyl group, and the other is a phenylene group.

6. A liquid crystal compound as claimed in claim 1, wherein the fluoroalkyl group bonded to the asymmetric carbon atom of the optically active center is a $CF_3$ group.

7. A liquid crystal compound as claimed in claim 1, wherein said compound is represented by formula:

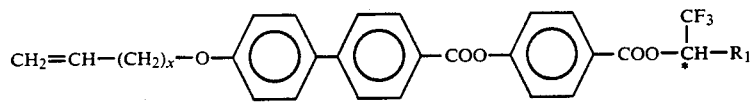

wherein $R_1$ is as defined in claim 1; and x is an integer of from 1 to 12.

8. A liquid crystal compound as claimed in claim 1, which exhibits $S^*(3)$ phase where the liquid crystal shows tristable states of molecular orientation.